United States Patent [19]

Eichenlaub, John E.

[11] Patent Number: 4,793,352
[45] Date of Patent: * Dec. 27, 1988

[54] LIMITED HEAT TRANSFER DEVICE AND METHOD

[76] Inventor: Eichenlaub, John E., 1300 France Ave. S., Golden Valley, Minn. 55427

[*] Notice: The portion of the term of this patent subsequent to Oct. 25, 2000 has been disclaimed.

[21] Appl. No.: 48,024

[22] Filed: May 11, 1987

Related U.S. Application Data

[63] Continuation of Ser. No. 827,780, Feb. 7, 1986, abandoned, which is a continuation of Ser. No. 537,499, Sep. 30, 1983, abandoned.

[51] Int. Cl.⁴ .................................................. A61F 7/00
[52] U.S. Cl. ..................................... 128/399; 128/402
[58] Field of Search ............... 128/203.17, 204.17, 128/303.1, 303.12, 367, 368, 399–403; 60/641.8

[56] References Cited

U.S. PATENT DOCUMENTS

| | | | |
|---|---|---|---|
| 697,181 | 4/1902 | Smith | 128/303.12 |
| 1,902,016 | 3/1933 | Copeman | 128/399 |
| 1,965,424 | 7/1934 | Mascedo | 128/402 |
| 2,077,453 | 4/1937 | Albright | 128/402 |
| 2,210,618 | 8/1940 | De St. Cyr | 128/402 |
| 2,617,420 | 11/1952 | Jozefoyk | 128/304 |
| 2,652,824 | 9/1953 | Hopp | 128/402 |
| 2,948,280 | 8/1960 | Vicik | 128/304 |
| 3,099,263 | 7/1963 | Palazzolo | 128/184 |
| 3,170,465 | 2/1965 | Henney et al. | 128/401 |
| 3,307,554 | 3/1967 | Thurnton et al. | 128/402 |
| 3,425,419 | 2/1969 | Dato | 128/402 |
| 3,580,795 | 5/1971 | Eichenlaub | 156/583 |
| 3,861,364 | 1/1975 | Greenfeld | 128/368 |
| 3,937,599 | 2/1976 | Thoreau et al. | 417/389 |
| 3,949,743 | 4/1976 | Shanbran | 128/203.17 |
| 4,292,971 | 10/1981 | Smith et al. | 128/256 |
| 4,353,359 | 10/1982 | Milbauer | 128/402 |
| 4,399,349 | 8/1983 | Deming et al. | 219/276 |
| 4,411,265 | 10/1983 | Eichenlaub | 128/400 |

FOREIGN PATENT DOCUMENTS 1212594 11/1970 United Kingdom ............... 128/400

OTHER PUBLICATIONS

"Apparatus for Heating of the Nasal Passages", Lwoff et al., Official Gazette, Aug. 1983.

Primary Examiner—Max Hindenburg
Attorney, Agent, or Firm—Schroeder & Siegfried

[57] ABSTRACT

Devices and methods for transferring heat to another object with close regulation of the maximum temperature obtainable. All embodiments utilize a vaporization unit wherein heat transfer material is vaporized. Vapors are directed to terminals where controlled heat transfer is effected through condensation heat loss. Terminals include devices for removing excess ear wax, providing physical therapy to body extremities and industrial, high temperature applications such as plastic welding. Condensate and excess vapor are under some circumstances reused through the use of a condensation unit.

26 Claims, 3 Drawing Sheets

LIMITED HEAT TRANSFER DEVICE AND METHOD

This is a continuation of application Ser. No. 827,780, filed Feb. 7, 1986, which is a continuation application of Ser. No. 537,499, filed Sept. 30, 1983, both of which are now abandoned.

BACKGROUND OF THE INVENTION

1. Field of the Invention

This invention relates to precisely controlled heat transfer devices and methods, which are particularly useful in medical applications requiring limited heat ranges.

2. Description of the Prior Art

Processes which require closely regulated heat typically rely on thermostatically controlled electrical resistance units and sophisticated safety relief valves and back-up systems. A controlled maximum temperature is desirable in many applications including medical treatment, welding of plastics, heat treatment of metals and the like.

Since heat can easily damage living tissue, many medical uses require means to limit heat transfer to avoid reaching temperatures which would otherwise cause harm. For example, paraffin baths and water vaporization devices may potentially reach unacceptable, dangerous temperature levels.

Traditional means of limiting heat transfer have several defects. Thermostatically controlled electrical resistance units such as heating pads vary substantially across their faces; a 15 to 20 degree Fahrenheit variation is quite common. Thermostatic control is difficult and expensive when applied in constricted places, such as the external ear canal. The transfer of heat by pumping thermostatically controlled electrically heated liquid through devices such as the aqua-K heating pad gives uniform control but it is quite expensive. This method does not adapt itself readily to confined spaces, since the liquid is difficult to force through a narrow passage at sufficient speed to make up for heat loss.

Other medical applications of heat transfer include the use of paraffin baths for heat treatment of arthritic joints. Paraffin baths require a large volume of paraffin which must be constantly heated to maintain its temperature. Paraffin is messy and coats any item placed within the bath. The baths are dependent on thermostatic heating controls to maintain a safe temperature. A stuck thermostat valve may result in excessively high temperatures. Such systems may result in heat damaged material or even in physical injury to a patient. Thermostatic control of temperature does not provide the safety required in such applications.

3. Brief Summary of the Invention

The limited heat transfer devices of the invention supply and provide vaporized liquid as a source of heat for heat transfer. A liquid is chosen with known boiling point and is placed within a suitable reservoir. The liquid is then heated to its vaporization point resulting in vapor having a known temperature. The temperature may be altered within the same liquid merely by altering the pressure of the system. Since pressure, volume and temperature are related by the formula $PV = nRT$, a change in pressure results in temperature change if the other variables remain fixed.

The vapor, while hot, represents the maximum temperature available under the system. The vapor is at a controlled upper temperature limit when it escapes from the reservoir as long as there is a source of liquid. The vapors are then directed through suitable conduits to a terminal area where accurately controlled heat transfer takes place.

While the device is useful for any application requiring heat transfer with closely regulated temperature and a maximum safety temperature, several embodiments are illustrated below.

One terminal area is designed to produce physical therapy results for the same purpose but to a better degree than paraffin baths, contrast baths and hot compresses. Vapor is introduced into a physical therapy terminal which comprises an enclosure designed like a glove box. A "glove" of thin plastic or rubber forms part of the enclosure such that a hand or other extremity thrust into the glove may be heated by vapors within the enclosure and exterior of the glove without contacting the vapors themselves.

Condensation occurs in an exothermic reaction over the entire affected surface of the glove, bringing the temperature to a uniform level at approximately the condensation point of the heat transfer material. As the condensate collects it is ultimately drained out through an outlet which may be connected to a return source of the heat transfer liquid.

A heating pad or hot compress terminal comprises an air mattress-like enclosure with a vapor inlet and a vapor outlet which are separated by seals. A valve produces a mild pressure backup to maintain vapor within the enclosure under slight pressure so that the passages remain expanded. A high degree of safety is achieved through the use of the closely controlled temperatures of the invention.

An ear wax removing terminal includes adjustable stop and gentle pressure applying members. Tubing is connected to the vapor supply for transmitting vapor to a tip portion which contacts excess cerumen in the external auditory canal. The controlled heat provided melts the wax plug allowing easy removal. Removal is accomplished by aspiration, absorption or by entrapment utilizing a retractable member adjacent the tip portion.

In any of the devices utilizing vapor heat transfer, an element for condensing surplus vapor may be added if the vaporization liquid is costly or hazardous.

A body cavity terminal for heat treatment of cavities including the vagina, rectum and the outer ear canal includes a vapor-tight, thin walled bag. Tubing is connected to the vapor supply for transmitting vapor to the bag for heat transfer. A vapor return tube with valving to allow the maintenance of low pressure to inflate the bag is connected to the condensation unit or allowed to escape to the air if the vapor is safe and inexpensive. Terminals intended for rectal use preferably have a narrow constriction to avoid discomfort within the anal canal.

Utilization of the heat transfer devices of the invention results in a clean, safe transfer of heat to the desired area. The use of vapors limits the maximum temperature obtainable and eliminates the need for thermostats and alarm and automatic shut-off systems.

BRIEF DESCRIPTION OF THE DRAWINGS

The detailed description of the invention, including its preferred embodiments, is hereinafter described with specific reference being made to the drawings in which.

DETAILED DESCRIPTION OF THE INVENTION Vaporization and Condensation Units

Figure 1:
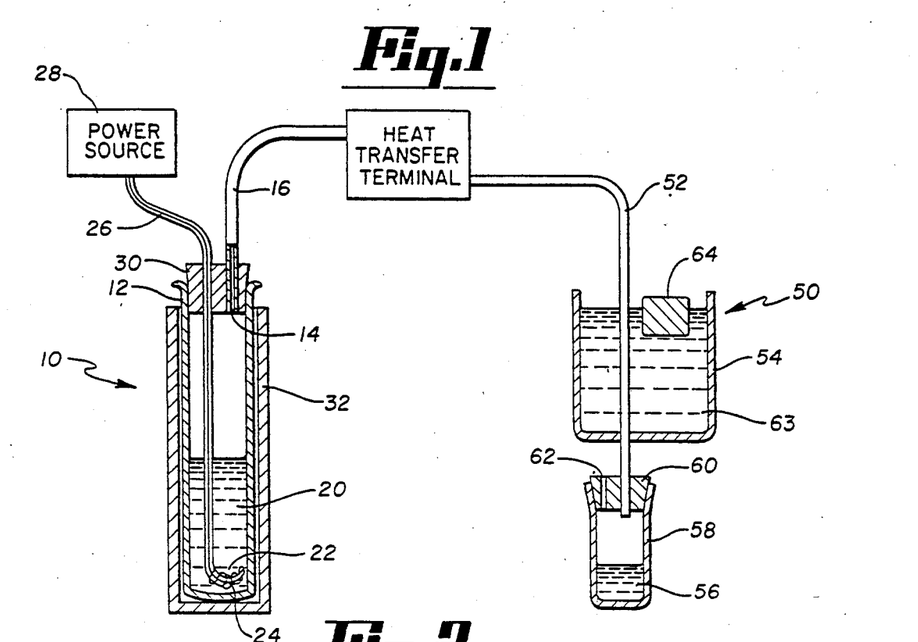
FIG. 1 is a side elevational view of the basic vaporization unit and vapor condensing unit with portions thereof shown in vertical section.

The basic unit common to all forms of the invention is shown in FIG. 1. It consists of two elements, a vaporization unit 10 and a condensation unit 50. The condensation unit 50 is not necessary in all applications. Recovery of condensation is desirable only if the materials used are costly or hazardous. Materials which are inexpensive, nontoxic and are not excessively flammable may be allowed to escape into the ambient air.

The vaporization unit 10 supplies hot vapor for conduction to the terminal areas, which will be discussed more fully below. Vaporization unit 10 includes heat transfer reservoir or container 12 which may be a tube or other suitable means to confine a heat transfer material in its liquid and vapor phase.

Container 12 includes a vapor outlet 14 which is connected to the terminal areas by tubing 16. Liquid 20 within container 12 is heated by a heating member which may be located outside container 12 or preferably inside as an immersion heater 22. Immersion heater 22 includes a wire 24 of an alloy such as those sold under the trademark Nichrome ® by Driver-Harris Co. of Harrison, N.J. or similar material which heats from passage of electricity through supply wire 26 that is supplied by current from source 28.

Source 28, in the preferred form, supplies a 12 volt DC current to wire 24 which vaporizes the heat transfer materials within container 12. A 12 volt, 1.5 amp transformer has been found to be suitable. Wraps of nichrome wire are formed until a rapid boil is produced without forcing closure means 30 off due to excessively rapid vaporization. Heating adjustments are based on the heat transfer material chosen.

As shown in FIG. 1, container 12 preferably includes closure means 30 which may be a rubber stopper through which vapor outlet 14, tubing 16 and wire 26 extend. Closure means 30 allows the introduction of replacement heat transfer fluid and facilitates cleaning and repair, if needed.

Container 12 is preferably surrounded by an insulating enclosure 32. Insulating enclosure 32 may be formed from a plastic pipe section with the lower end sealed.

Heat transfer material in liquid phase 20 is heated by heating means 22 to its vaporization point and exits through vapor outlet 14, becoming available for heat transfer at a terminal attached to tubing 16.

Vapor condensation unit 50 receives used vapor from the attached terminal area through ducting 52 which passes through condenser 54 where heat is extracted, causing the vapor to condense. Condensate 56 passes from ducting 52 into condensate reservoir 58 which may include stopper 60 and vent 62 to the atmosphere. Condenser 54 may be of any commercially available type or as simple a device as a container of cooling water 63 including ice 64, as shown schematically in FIG. 1.

Figure 7:
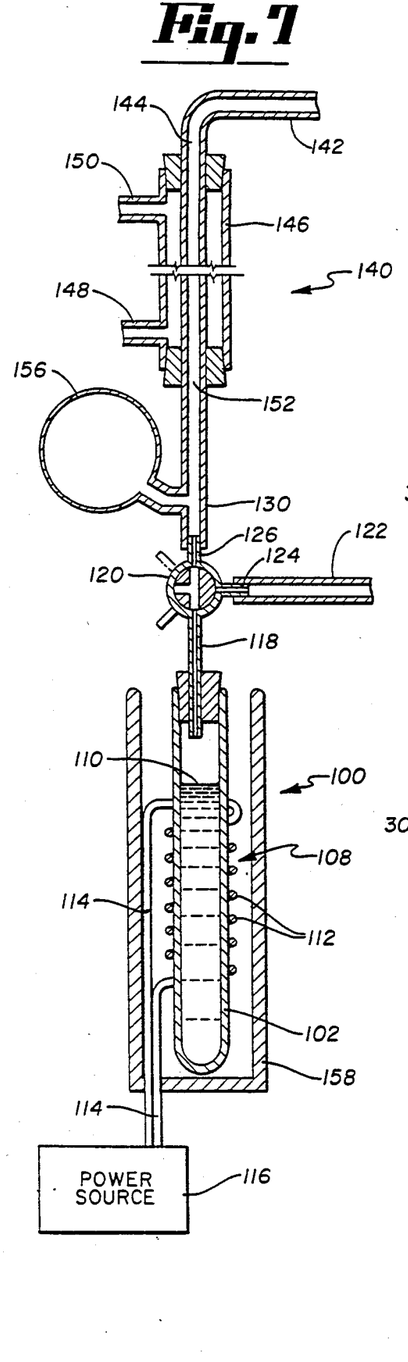
FIG. 7 is a side elevational view of the preferred embodiment of a vaporization unit and vapor condensing unit for sealed systems with portions thereof shown in vertical section.

The preferred vaporization and condensation unit for use with heat transfer materials requiring sealed systems is shown in FIG. 7. Acetyl chloride has a boiling point of 50.9° C. at atmospheric pressure, which is an ideal condensation point for limited heat transfer in many physical therapy applications. However, since acetyl chloride decomposes violently in the presence of moisture, it must be used in a sealed system as shown in FIG. 7.

The sealed system includes vaporization unit 100 which comprises a heat transfer reservoir 102, vapor outlet 104, sealing member or stopper 106 and heater 108.

Heater 108 preferably supplies heat to heat transfer material 110 within reservoir 102 by the use of a nichrome wire wrap 112 wound around reservoir 102. Power supply wire 114 connects to nichrome wire wrap 112 and power supply 116.

Vapor generated by heat from wire wraps 112 passes through vapor outlet 104 and ducting 118 which is in fluid tight communication with outlet 104. Ducting 118 is in fluid tight communication with three way valve 120. Vapor supply ducting 122 attaches to valve port 124 such that vapor passes therethrough when valve 120 is positioned to open port 124. Various terminals are attached by vaportight means to duct 122. Valve port 126 is in fluid tight communication with condensation unit 140 through duct 130.

Return vapor and condensate flows from the attached terminal through flexible tubing 142 to condenser inlet 144. Vapor and condensate enters condenser 146 and passes through a tube within a jacket of cold fluid. The cooling fluid is supplied through inlet 148 and exits through outlet 150. Condensate drains from condenser 146 through condenser outlet 152 and enters duct 130 which also acts as a temporary reservoir of condensate. Expansion of air and vapor within the system is achieved through the use of flexible or elastic bag 156 attached to ducting 130 below condenser 146. Elastic bag 156 is normally in a collapsed state when the vaporization and condensation units are not in use.

During operation, expansion bag 156 and ducting 130 collect condensate as vapor passes through condenser 146. Heater 108 is shut off manually before all of the heat transfer material within reservoir 102 is vaporized. When the heat transfer material stops boiling, the operator moves three way valve 120 to create a sealed passage from duct 130 through valve port 126 to ducting 118 and reservoir 102. The suction created by the cooling heat transfer material in reservoir 102 aids the return of condensate from ducting 130 and expansion bag 156.

All of the components of the vaporization and condensate units are designed such that the system is sealed from atmospheric air. Preferably, reservoir 102 is insulated with an insulating jacket 158 to limit heat loss to the atmosphere.

Heat Transfer Terminals

The terminals referred to above receive vapor through tubing 16 or ducting 118. The terminals are the site where heat transfer takes place, with the heat of condensation becoming available to heat an object at the terminal. Cooled vapor or condensate passes from the terminal to flexible tubing 142, ducting 52 or is lost to the surrounding atmosphere if it is non-toxic and inexpensive. Each terminal therefore employs a vaporization unit and may or may not employ a condensation unit, depending upon the transfer material being utilized.

Ear Wax Removing Terminal

Excess ear wax or cerumen must be removed to prevent hearing impairment, pain, itching, discharge or indigestion. Traditional remedies to remove serious accumulations of wax often involve the use of a warm water flush.

My Ear Wax Removing Device application, U.S. Ser. No. 275,209 filed 6/19/81 as a continuation of my application U.S. Ser. No. 049,179 filed 6/18/79, now allowed, which is incorporated herein by reference, discloses the problems encountered in prior art devices and discloses an ear wax removing device which uses warm fluid which does not immediately contact the ear or wax to heat the wax removing device.

The ear wax removing device of application, U.S. Ser. No. 275,209 may be utilized as a terminal to be attached to the vaporization and condensation units of this application. For sake of clarity, the reference numerals of application U.S. Ser. No. 275,209 appear herein with primes (') to distinguish them from reference numerals utilized above.

Conduit 31' as shown in my above patent application may be directly connected to vaporization tubing 16 or ducting 118 such that vapors from the vaporization unit pass into conduit 31' and curette 13'. Returning vapor passes through flexible return conduit 39' which in turn communicates with condensation unit ducting 52 or flexible tubing 142. Such a terminal results in an ear wax removing device that eliminates the need for heating controls and prevents damage to the ear by eliminating a source of potentially too hot water.

Figures 2, 3:
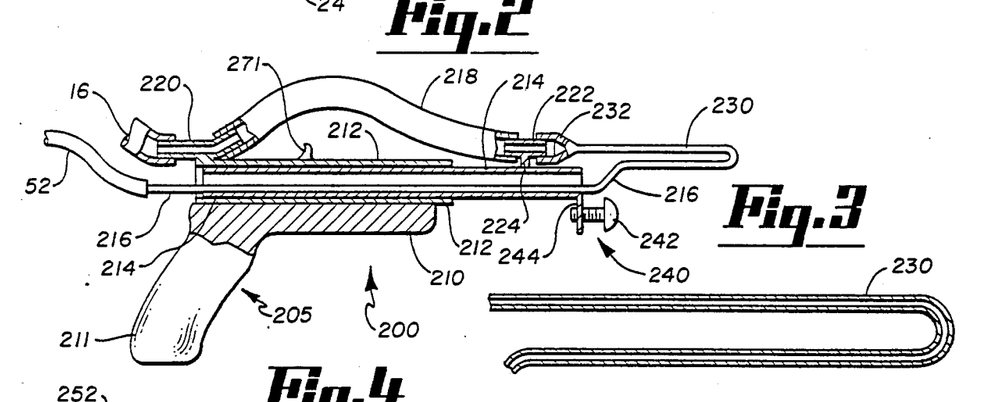
FIG. 2 is a side elevational view of the preferred form of my ear wax removing terminal with portions thereof in vertical sections.
FIG. 3 is a partial vertical sectional view on an enlarged scale of the tip portion of my ear wax removing terminal of FIG. 2.

The preferred ear wax removing terminal 200 is shown in FIG. 2. Terminal 200 includes a mounting plate 205 which, as shown, is pistol shaped and has a forward end portion 210 and rear end portion 211 extending at right angles to its general plane. Rigid hollow tube 212 is rigidly mounted to the top of mounting plate 205. End 215 of rigid tube 214 carries rigid vapor return tube 216 within its bore such that condensation unit ducting 52 or flexible tubing 142 may be attached in fluid communication to vapor return tube 216. Ducting 52 and tubing 142 are preferably formed of a flexible tubing such as the vinyl compounds sold under the trademark TYGON by National Lead Co. Rigid tube 214 moves freely within the longitudinal axis of tube 212 in a telescoping, sliding relation. Vapor return tube 216 is mounted within tube 214 in a fixed, nonsliding position.

Vapor supply tubing 218 formed of flexible, elastic tubing such as rubber or Tygon ® brand vinyl compounds is attached in fluid communication with brass tube 220. Tubing 218 should be able to bend at up to a ninety degree angle without collapsing or kinking. Brass tube 220 is fixedly mounted to rear end portion 211 of mounting plate 210. Brass tube 220 is in fluid communication with vapor supply tubing 16 or ducting 118 of vaporization unit 10 or 100. Tubing 16 or ducting 118 is preferably formed of a flexible, insulative tubing such as polyethylene or vinyl compounds sold under the trademark Tygon by National Lead Company.

The other end of flexible vapor supply tube 218 is secured in fluid tight communication to a brass connecting tube 222, which is fixedly mounted to rigid tube 214 along the forward end portion 210 of rigid tube 214 by means of brass block 224.

Curette 230 which is tubular in form and may be formed of any suitable material is attached at end 232 to connecting tube 222. As shown in FIGS. 2 and 3, curette 230 may be formed from 25 gauge hypodermic needle tubing, with the hub of the needle forming end 232. Curette 230 is bent into a U-shaped metal tube such that end 234 is attached in fluid tight communication with vapor return tube 216.

As used herein, "curette" is not limited to a spoon shaped device for removing wax from a cavity. Curette, as used herein, is the heat transfer tip wherein the heat of condensation passes from the vapor to the area to be heated. Vapor passes through a conduit within the curette. The curette may additionally function as a scraping tool due to its shape.

Penetration-controlling stop 240 is attached at the end of rigid tube 214. The broad head of stop 240 impinges on the conch, the depression adjacent to the ear canal, limiting the penetration depth of curette 230. Preferably, stop 240 is adjustable, consisting of a rubber covered screw 242 threaded through flange 244 at the end of tube 214.

Brass block 224 acts as a spacer from tube 214 to permit attachment of flexible tubing 218 and curette 230 to brass connecting tube 222. Brass block 224 also separates the axis of curette 230 sufficiently from the axis of penetration—controlling stop 240 to make stop 240 impinge correctly in the hollow of the outer ear. Brass tube 224 also ensures that curette 230 moves as a unit with tube 214.

In operation, flexible tube 218 is arched such that its elastic recoil urges curette 230 forward, applying gentle pressure against a wax plug within the ear. The arching of flexible tube 218 is achieved by angling tube 220 upwardly and by selecting tube 218 length which is longer than the straight line distances between tube 220 and tube 222. The arching and elasticity of tube 218 supplies gentle pressure to exert against a wax plug. Flexible tube 218 conveys vapor to curette 230 to melt the cerumen. Using methanol as the heat transfer material, with a boiling point of 64.96° C. and without insulating the terminal 200, curette 230 temperatures ranged from about 48° C. to about 52° C. which is ideal for applications within the ear.

The use of acetyl chloride (which has a boiling point of 50.9° C.) for the same purposes requires a sealed system as shown in FIG. 7. Terminal portions 200 carrying vapor are covered with a layer of insulating material with the exception of curette 230. Curette temperatures closely approached the 50.9° C. maximum obtainable, providing a safe, effective temperature and upper limit.

Physical removal of ear wax involves either aspiration of melted wax, absorption or entrapment. Various embodiments for such are shown in FIGS. 4, 5 and 6.

Figures 4, 5, 6:
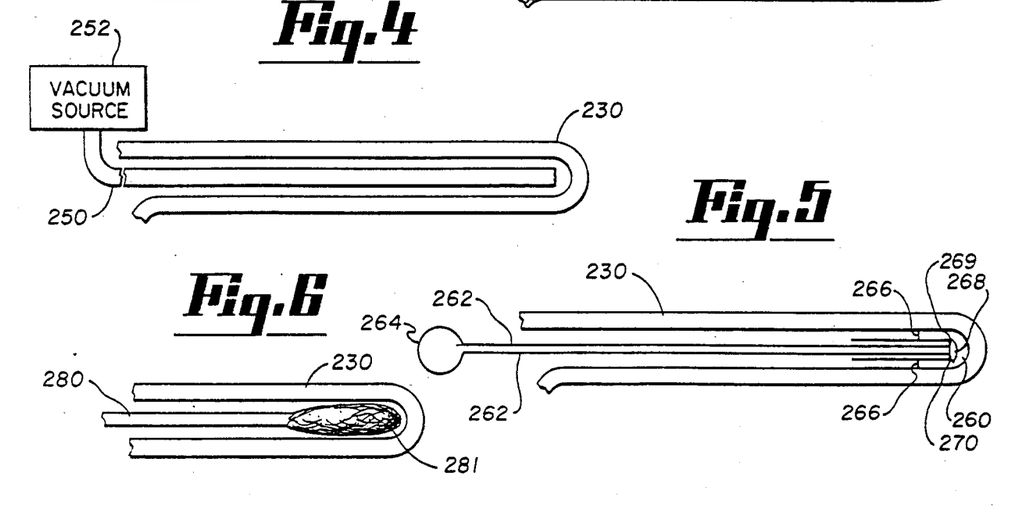
FIG. 4 is a side elevational view on an enlarged scale of the tip portion of my ear wax removing terminal of FIG. 2 including an aspirator.
FIG. 5 is a side elevational view on an enlarged scale of the tip portion of my ear wax removing terminal of FIG. 2 with an expandable umbrella-like wax extractor.
FIG. 6 is a side elevational view on an enlarged scale of the tip portion of my ear wax removing terminal of FIG. 2 with an absorbent applicator.

In FIG. 4, wax is removed by aspiration as soon as it is melted. Tube 250 is attached in close thermal contact with the vapor supply leg of U-shaped curette 230 and terminates just inside the U. It is attached by non-collapsible means to an aspirator 252 shown generally in block form. Aspiration is particularly useful for professional use under direct vision through an otoscope. The curette 230 and attached aspirator tube 250 may be bent into various shapes for convenient removal of cerumen from difficult to reach areas such as stapdectomy and mastoid cavities. Conventional medical aspirators are suitable.

In FIG. 5, wax is removed with the aid of an expandable, umbrella-like device 260. Device 260 comprises a filament of fine wire 262 bent into a handle 264 at its distal end and sharply reversed upon itself just short of the U-shaped end of curette 230. Wire 262 is attached to one side of U-shaped curette 230 by a weld 266 or other suitable means. A piece of pliable, delicate sheeting 268, such as latex rubber or polyethylene, is attached to wire 262 at each wire reversion point 269, 270 near the end of curette 230. Sheeting 268 is formed such that its outer diameter, when expanded, is approximately equal to that of the external auditory canal. Sheeting 268 is ribbed such that it assumes a disc-shaped configuration when its attachment points to wire 262 are spread apart.

Movement of handle 264 toward the distal end (away from curette 230) causes reversion points 269, 270 to separate. This expands sheeting 268 into an umbrella-like structure which, when pulled out of the ear canal, pulls wax with it assuming the warm curette 230 has melted through the wax plug and the tip extends into or beyond the interior of the plug. Handle 264 may be held in the distal, umbrella open position for wax removal by passing handle loop 264 over projection 271 extending from mounting plate 205 as shown in FIG. 2.

In FIG. 6, wax is removed by means of a cotton-tipped, or other absorbent-tipped applicator 280 placed just within the U formed by U-shaped curette 230. Wax melted by vapor heated curette 230 is absorbed while still in liquid condition onto the cotton 281 of applicator 280. When the applicator becomes saturated, it is withdrawn and replaced with another, similar applicator. Cotton may less preferably be attached directly to curette 230.

Hot Compress Terminal

Heating pads that rely on electrical heat may develop hot spots, vary in temperature, and have other disadvantages. Traditional hot water bottles may be excessively warm and tend to cool down too quickly.

Figure 8:
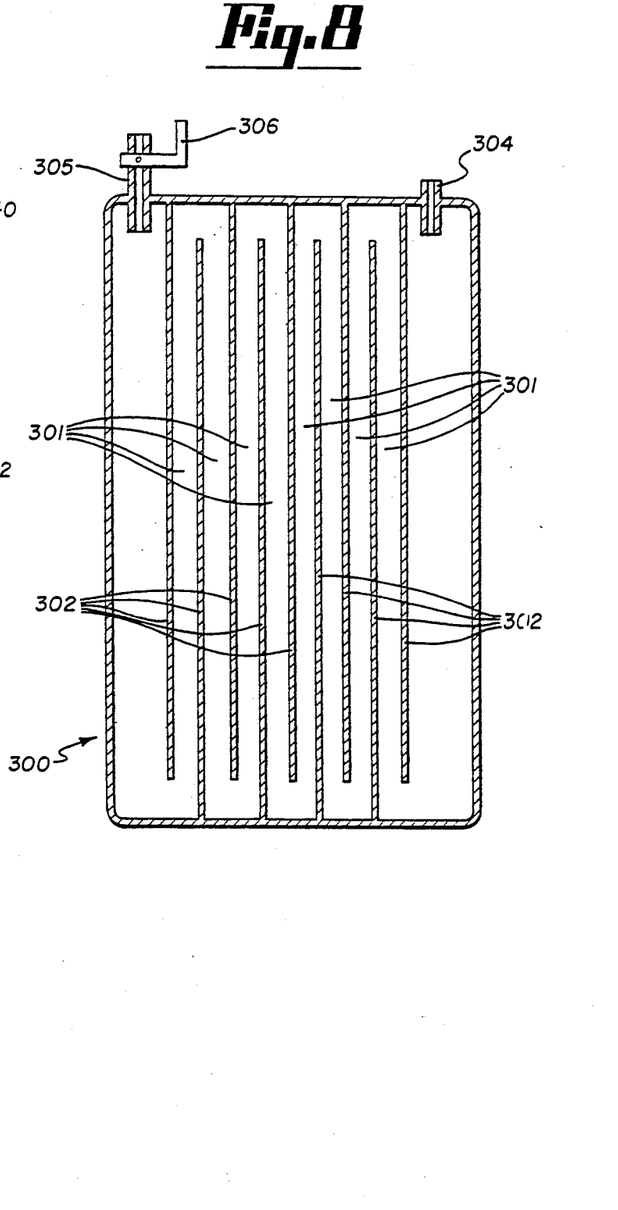
FIG. 8 is a top plan view of my heating pad terminal.

The utilization of vapors from the vaporization unit of the invention in combination with vapor heated compress terminal 300 provides heat transfer with a safe, predetermined upper temperature limit. Compress terminal 300 is composed of a flexible plastic or rubber enclosure with a series of communicating inner chambers 301 defined by a pattern of seals 302 extending between the walls of the terminal as shown in FIG. 8. Vapor from vaporization unit 10 or 100 enters inlet 304 to which tubing 16 or vapor supply ducting 122 is connected. Vapor passes through the connecting chambers and exits through outlet 305. Valve 306, preferably a rubber flutter-valve or other device for producing mild pressure backup, keeps vapor within the terminal under low pressure such that chambers 301 remain expanded. Outlet 305 may either allow non-toxic, inexpensive heat transfer material vapors to escape or recycle the vapors by connection to condenser ducting 52 or tubing 142.

Physical Therapy Terminal

Figures 9, 10, 11:
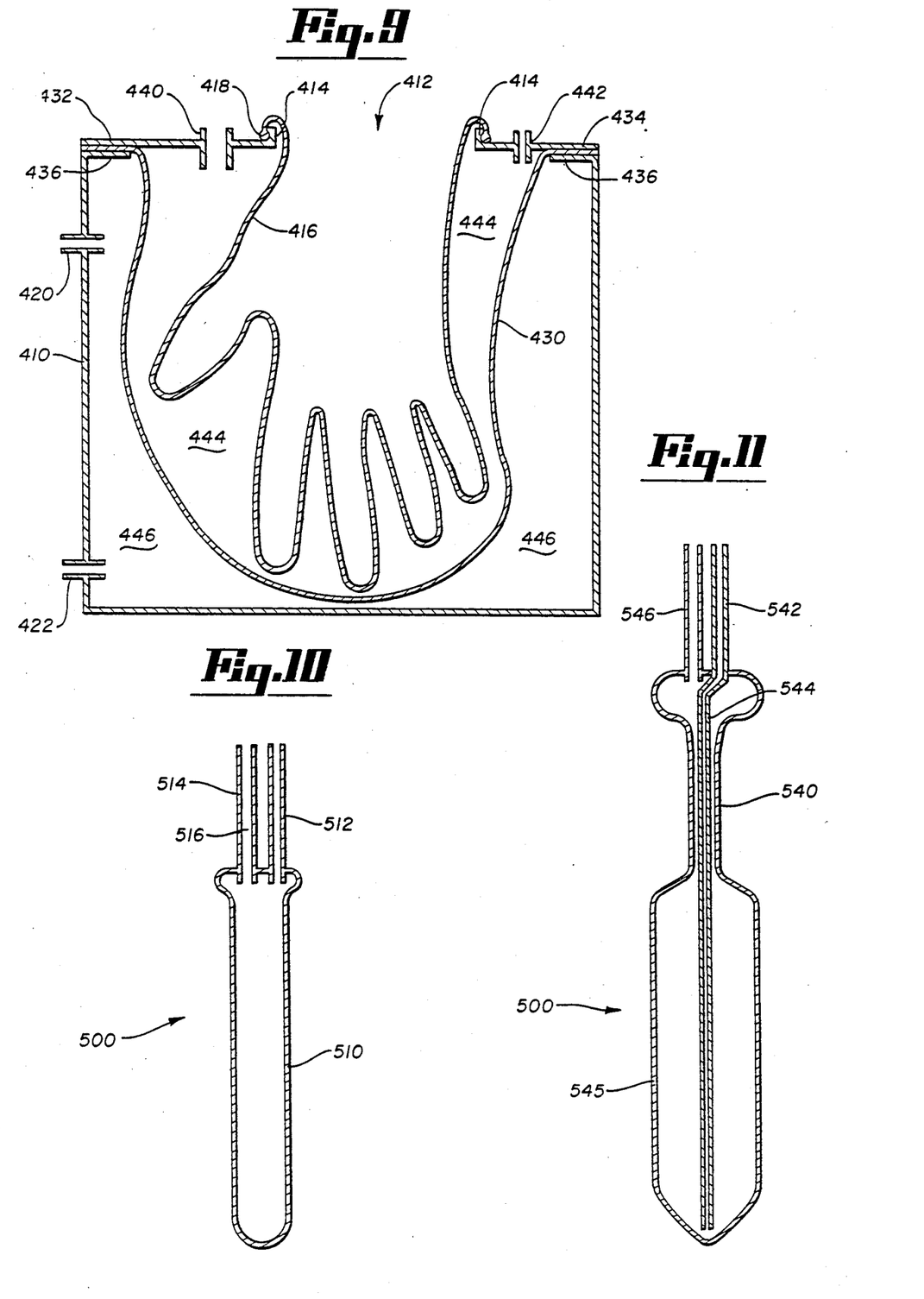
FIG. 9 is a side elevational view of a physical therapy terminal shown in vertical sections.
FIG. 10 is a view of a body cavity terminal in vertical section.
FIG. 11 is a view of a body cavity terminal with a narrow portion in vertical section.

As a replacement for paraffin baths wherein the afflicted body part is immersed in molten paraffin, vapor from vaporization unit 10 or 100 provides heat transfer through physical therapy which, as shown, has a non-pressurized interior in fluid communication with the atmosphere. Terminal 400, as shown in FIG. 9, generally consists of enclosure 410 which includes opening 412 with an upstanding retaining flange 414. A heat transfer membrane 416, such as a thin rubber, latex or plastic glove is inserted into enclosure 410 with the membrane margin 418 rolled over retaining flange 414 in a sealed relationship. The seal may be made by virtue of elastic properties of membrane 416 or by other means including hose clamps.

Vapor inlet 420 enters enclosure 410 and is connected to vaporization unit 10 or 100 by tubing 16 or ducting 122 respectively. Vapor and condensate exits enclosure 410 through outlet 422 which may lead to a floor drain (not shown) or more preferably to condenser 154 or 146 through ducting 52 or tubing 142 respectively. If desired, a valve on outlet 422 may supply low back pressure within enclosure 410 as described above for hot compress terminal 300.

Preferably, physical therapy terminal 400 includes means to cool the object inserted into membrane 416. A second, flexible thin membrane 430 surrounds first membrane 416 within the enclosure and is held in sealing relation between enclosure top 432, 434 and enclosure flange 436. A cold water inlet 440 and cold water outlet 442 supply chilling water into the space 444 defined between membrane 416 and membrane 430. The remaining area within enclosure 410 defines vapor chamber 446.

In operation, a heating phase is applied to an extremity, such as a hand thrust into membrane or glove 416 by supplying warm vapors into enclosure 410. When used as a contrast bath, heating is discontinued and cold water chills the extremity within membrane 416 for the desired time period. Transmission of heat into and out of the extremity is readily accomplished due to the thinness of membranes 416 and 430. During heating, residual water in space 444 is drained due to inversion aided by a constriction or valve in vapor outlet 422. Cold water confining membrane 430 collapes against membrane or glove 416 when the water is drained from space 444 allowing heat transmission. Heat transfer is accomplished through the exothermic reaction of condensation on the membranes surrounding the extremity. The maximum temperature an extremity is subjected to is approximately the condensation point of the heat transfer material chosen.

Body Cavity Terminal

The limited heat transfer achieved through the use of vapors may desirably be utilized for heat treatment within body cavities.

FIG. 10 shows body cavity terminal 500, which is composed of a vapor-tight, flexible, thin bag 510 which is preferably formed of polyethylene. The thinness of bag 510 allows the transfer of heat to the tissue. Inlet tube 512 is attached in fluid communication with the interior of bag 510 as shown in FIG. 10. Inlet tube 512 is connected to vaporization unit 10 or 100 such that vapors fill bag 510.

An outlet tube 514 allows vapors to exit bag 510. Moderate pressure is maintained within bag 512 due to the addition of a rubber flap valve 516 or other suitable means for producing back pressure.

Bag 510 expands within the treated body cavity until it comes into substantial contact with the surrounding tissue walls. The thinness and flexibility of bag 510 provides greater surface area contact to maximize heat transfer effectiveness.

As shown in FIG. 11, body cavity terminal 500 may be designed with a narrow neck portion 540. Heating of the rectum and prostate may preferably utilize a narrow neck 540 to permit terminal 500 to lie within the anal canal without creating discomfort. Inlet tube 542 connects to a semi-rigid tube 544. The inward portion of tube 544 is attached to bag 545 to one wall to aid in the introduction of terminal 500 and to conduct vapors to the far end of bag 545.

Vapor exits the rectal body cavity terminal through outlet tube 546. Vapor is maintained within bag 545 by external sphincter pressure at narrow neck 540.

In all forms of body cavity terminal 500, exiting vapor may escape freely to the air or return to a condensation unit as described above.

The use of heat in any medical application of the limited heat transfer device of the invention contemplates heat transfer at a temperature below that which will damage living tissue. At the heat transfer surface itself, the temperature should be at least about 32° C. and no higher than about 57° C. Standard "hot" applications may utilize a maximum temperature of about 52° C. which is below the tissue damage point.

Preferably, the maximum temperature that contacts tissue should be below a patient's discomfort point. The discomfort point is somewhat lower than the tissue damage point, discomfort instead being measured by a patient's individual pain threshold.

It has been found that heat transfer materials whose vaporization point exceeds both the discomfort and tissue damage points may be employed by designing heat loss within the system. For example, methanol with a vaporization point of about 65° C. has been used with the ear wax removal terminal of the invention. Heat is lost through the uninsulated tubing and U-shaped curette tube such that the external temperature of the curette is within a medically safe temperature range. It is believed that heat transfer materials with vaporization points as high as about 80° C. may be used if enough heat loss is designed into the system.

Safe, effective transfer of heat to tissue is possible within body cavities through the use of the vaporization units and the heat transfer terminals of the invention. Heat transfer is clean and the maximum temperature limit depends on the chemical chosen rather than on thermostatically controlled valves, annunciators and other electrical devices.

Plastic Welding Terminal

In my U.S. Pat. No. 3,580,795, entitled "Apparatus for Welding Heat Sealable Sheet Material" which is incorporated herein by reference, I described a heat and pressure transmissive hollow head with a wall of fiberglass reinforced polytetrafluorothylene. The patent's device uses circulating fluids heated to a thermostatically controlled level to exert uniform pressure and transmit uniform heat to materials interposed between the flexible head and a solid, insulated base.

The head of U.S. Pat. No. 3,580,795 may be utilized as a plastic welding terminal utilizing vapor supplied by the vaporization unit of the invention. The vapor is used at several pounds per square inch pressure eliminating theremostatic controls. Outflow from the terminal is condensed in a condensing unit.

Heat Transfer Materials

In any of the terminals described herein, changing the pressure within the system will alter the heat transfer material's boiling point resulting in a vapor at a different temperature. Thus, nearly any temperature may be selected by choosing a heat transfer material and adjusting its boiling point by pressure change. Suitable heat transfer materials for medical purposes include methyl silicane, carbon disulfide, isopropyl nitrite, allyl methyl ether, cyclopentane, cyclopentene, propional fluoride, acetyl chloride, dimethyl selenide, hydroxylamine, methyl acetate, isopropyl vinyl ether and methanol. For applications requiring higher temperatures, such as plastic welding, metal treating and other industrial processes, carbon tetrachloride, fluorophosphoric acid, selenium oxyfluoride, aluminum ethoxide, aluminum propoxide, sodium amide and lead bromide may be utilized. Other available or synthesized chemicals may be utilized with the invention to provide a wide range of precisely regulated temperatures for heat transfer.

In considering this invention, it should be remembered that the present disclosure is illustrative only, and that the scope of the invention should be determined by the appended claims.

What is claimed is:

1. A vapor-utilization device for heating human body tissue without danger thereto at or below a predetermined maximum temperature, comprising:
    (a) vaporization means for heating a liquid within a chamber to produce vapors;
    (b) vapor transfer means connected to said vaporization means in non-diluting vapor-conducting relation for directing said vapors in non-diluted condition to a heating terminal; and
    (c) a heating terminal having throughout its extended use a normally non-pressurized interior in free fluid communication with the atmosphere and being connected to said vapor transfer means in non-diluted vapor-receiving relation and including a heat conductive surface which allows the heat of condensation to transfer from said vapor across said surface, said heating terminal comprising a heating chamber with a vapor inlet and outlet and a flexible, heat transmitting glove in sealed relationship within said heating chamber such that an object may be inserted into said glove within said heating chamber.

2. The device of claim 1 wherein said heating chamber further includes a flexible bag surrounding said glove, and a water inlet and outlet connecting a supply of cooling water to the space defined between said flexible bag and glove within said heating chamber.

3. An ear wax removing device comprising:
    (a) a mounting member;
    (b) a curette having a hollow interior and rigid exterior surfaces movably mounted on said mounting member for forward and rearward longitudinal movement relative thereto and having a forward end portion and rearward end portion;

(c) said curette having fluid passages defined within the hollow interior through which vapor may be circulated;

(d) liquid vaporization means for providing a source of vaporized liquid;

(e) vapor circulating means connected to said vaporization means and curette in fluid circulating relation for passing vaporized liquid through said curette thereby warming said curette;

(f) curette mounting means movably connecting said curette to said mounting member; and (g) pressure applying mechanism carried by said curette mounting means and connected to said curette in pressure-transmitting relation for continuously but gently urging said curette forwardly.

4. An ear wax removing device comprising:
(a) a mounting member;
(b) a rigid, heated ear wax softening curette movably mounted on said mounting member for forward and rearward longitudinal movement relative thereto and having a forward end portion and rearward end portion;
(c) a pressure applying mechanism mounted on said mounting member separate from said curette and connected to said curette for gently urging said curette forwardly relative to said mounting member;
(d) curette-penetration limiting means carried by said mounting member for limiting the extent to which said curette may be inserted in the ear;
(e) liquid vaporization means for providing a source of vaporized liquid;
(f) vapor circulating means connected to said vaporization means and curette in fluid circulating relation for passing vaporized liquid through said curette and effectively warming said curette; and
(g) wax removing means constructed and arranged to be utilized with said curette for removing ear wax after it has been warmed by said curette.

5. The ear wax removing device of claim 4 wherein said liquid vaporization means includes a vaporization container, liquid, and heating means in heat transmitting relation with said liquid in said vaporation container and a vapor outlet in fluid communication with said vaporization circulating means.

6. The ear wax removing device of claim 5 wherein said heating means includes power supply wire and nichrome wire in heat transmitting relation with said vaporization container.

7. The ear wax removing device of claim 5 wherein said vaporization container and vaporization circulating means are insulated such that a known heat loss is achieved in order to select the curette temperature in relation to the boiling point of said liquid.

8. The ear wax removing device of claim 4 wherein said curette is a U-shaped heat conductive tube having a hollow interior and rigid exterior surfaces, and having a supply leg of said U-shaped tube connected in fluid circulating relation to said vaporization circulation means.

9. The ear wax removing device of claim 8 wherein said U-shaped heat conductive tube includes a return leg, said return leg being connected in fluid communication with said condensation means for condensing said vapor into a liquid and for collecting said condensed vapor.

10. The ear wax removing device of claim 9 wherein said condensation means includes a condensor in fluid conductive relation with said curette return leg, an air expansion chamber and a condensate reservoir.

11. The ear wax removing device of claim 10 wherein said condensate reservoir is constructed and arranged such that a valve connected between said reservoir and said vaporization container allows condensate to return to said vaporization container when said valve is opened.

12. The ear wax removing device of claim 4 wherein said wax removing means is constructed and arranged such that a hollow tube placed adjacent said curette removes wax by an aspirator.

13. The ear wax removing device of claim 4 wherein said ear wax removing means includes an absorbent tipped applicator swab which absorbs wax melted by said curette.

14. The ear wax removing device of claim 4 wherein said ear wax removing means includes a retractable member which passes through a wax plug with said curette, and when said retractable member is extended, pulls wax out of the ear when said ear wax removing device is removed from the ear.

15. A method for closely controlling heat transfer to living tissue which limits the maximum temperature of a transfer agent comprising:
(a) heating a heat transfer liquid to its boiling point to produce vapor, said heat transfer liquid having a boiling point below the tissue damage point;
(b) sustaining said liquid at its boiling point;
(c) directing said vapor through conduits to a heat transfer agent terminal; and
(d) heating said living tissue by placing said heat transfer agent terminal in heat transmissive relation to said tissue such that same is warmed due to the heat of condensation.

16. The method of claim 15 wherein said heat transfer liquid has a boiling point temperature below a physical discomfort point.

17. The method of claim 15 wherein said heat transfer liquid has a boiling point temperature between about 32° C. and 57° C.

18. The method of claim 15 wherein said heat transfer agent terminal has each of the elements of the heating terminal of claim 1.

19. The method of removing excess ear wax comprising:
(a) heating a liquid to its boiling points to produce vapor;
(b) sustaining said liquid at its boiling point;
(c) passing said vapor through a heat conductive tube;
(d) inserting said heat conductive tube within an ear until said tube contacts excess ear wax;
(e) removing said ear wax when said wax is liquefied by heat; and
(f) removing said heat conducting tube from said ear.

20. The method of claim 19 wherein vapor from said heat conductive tube is condensed and returned to a closed reservoir.

21. The method of claim 20 wherein said vapor is condensed by the application of fluid at a temperature below the vapor's boiling point to a return side conduit connected to said heat conductive tubing.

22. The method of claim 21 wherein said liquid is acetyl chloride.

23. The method of claim 22 wherein said liquid and vapors are contained within a closed system such that acetyl chloride is not exposed to a patient.

24. The method of claim 19 wherein said liquid is selected from the group consisting of methanol and acetyl chloride.

25. The method of claim 19 wherein said liquid has a boiling point greater than about 37° C. and less than about 70° C.

26. The method of claim 19 wherein said liquid has a boiling point below a tissue damage point.

* * * * *

UNITED STATES PATENT AND TRADEMARK OFFICE
CERTIFICATE OF CORRECTION

PATENT NO. : 4,793,352
DATED : December 27, 1988
INVENTOR(S) : John E. Eichenlaub It is certified that error appears in the above-identified patent and that said Letters Patent is hereby corrected as shown below:

Column 3, line 29, insert "neck" after "narrow"

Signed and Sealed this

Thirteenth Day of June, 1989

Attest:

DONALD J. QUIGG

*Attesting Officer*  *Commissioner of Patents and Trademarks*